(12) United States Patent
Visser

(10) Patent No.: US 8,519,999 B2
(45) Date of Patent: Aug. 27, 2013

(54) METHOD OF PRODUCING AND DISPLAYING AN IMAGE OF A 3 DIMENSIONAL VOLUME

(75) Inventor: Cornelis Pieter Visser, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 1541 days.

(21) Appl. No.: 10/512,721

(22) PCT Filed: Apr. 11, 2003

(86) PCT No.: PCT/IB03/01534
§ 371 (c)(1),
(2), (4) Date: Oct. 29, 2004

(87) PCT Pub. No.: WO03/094114
PCT Pub. Date: Nov. 13, 2003

(65) Prior Publication Data
US 2005/0174347 A1    Aug. 11, 2005

(30) Foreign Application Priority Data
May 3, 2002    (EP) ..................... 02076764

(51) Int. Cl.
G06T 15/10    (2011.01)
G06T 15/20    (2011.01)

(52) U.S. Cl.
USPC ............ 345/427; 345/419; 345/420; 382/131

(58) Field of Classification Search
USPC ....................................................... 345/427
See application file for complete search history.

(56) References Cited

U.S. PATENT DOCUMENTS

| | | | | |
|---|---|---|---|---|
| 5,734,384 A * | 3/1998 | Yanof et al. | ........... | 345/424 |
| 6,064,904 A * | 5/2000 | Yanof et al. | ........... | 600/414 |
| 6,112,750 A * | 9/2000 | Chandra | ........... | 128/898 |
| 6,529,758 B2 * | 3/2003 | Shahidi | ........... | 600/407 |
| 6,557,558 B1 * | 5/2003 | Tajima et al. | ........... | 128/897 |
| 6,671,538 B1 * | 12/2003 | Ehnholm et al. | ........... | 600/425 |
| 6,675,037 B1 * | 1/2004 | Tsekos | ........... | 600/417 |
| 2003/0108145 A1 * | 6/2003 | Knoplioch et al. | ........... | 378/4 |
| 2004/0034300 A1 * | 2/2004 | Verard et al. | ........... | 600/424 |

OTHER PUBLICATIONS

Gering, D., Nabavi, A. Nabavi, Kikinis, R., Hata, N., Odonnell, L., Grimson, W., Jolesz, F., Black, P., Wells III., W., An Integrated Visualization System for Surgical Planning and Guidance Using Image Fusion and an Open MR, Jun. 2001, Journal of Magnetic Resonance Imaging, vol. 13, pp. 967-975.*

(Continued)

*Primary Examiner* — Said Broome

(57) ABSTRACT

An image of a multi-dimensional volume from a multi-dimensional object data set is displayed on a monitor, a target point and a surface are identified, a target centric projection is then created by projecting information from the target point onto the identified surface. Critical volumes are identified within the multi-dimensional volume and information from these is projected onto the identified surface. Points are selected on the surface and a rectilinear pathway calculated between the selected points and the target point. Distance information between the target point and the identified surface is calculated for selected points. Distance information is projected onto the identified surface. The critical volumes are enlarged prior to projection. The projection may be produced around a selected point on the surface and displayed together with the multi-dimensional volume.

9 Claims, 7 Drawing Sheets

(56) References Cited

OTHER PUBLICATIONS

Gering, D., A System for Surgical Planning and Guidance using Image Fusion and Interventional MR, Dec. 1999, Masters thesis, Massachusetts Institute of Technology, pp. 1-106.*

3D Modelling for Computer-Assisted Neurosurgical Procedures by S. M. Krishnan et al., Biomedical Engineering, Applications, Basis and Communications, vol. 7, No. 5, 1995.

Novins, K. L., et al.; An Efficient Method for Volume Rendering Using Perspective Projectionl; 1990; Computer Graphics; 24(5)95-102.

* cited by examiner

METHOD OF PRODUCING AND DISPLAYING AN IMAGE OF A 3 DIMENSIONAL VOLUME

The invention relates to a method of producing and displaying an image of a multi-dimensional volume from a multi-dimensional object data set, the method comprising the identification of a target point within the multi-dimensional volume.

The meaningful display of 3 dimensional image data is important in many areas of technology. Modern imaging methods allow the reconstruction and visualization of many objects and can be particularly useful in medical imaging. Imaging methods are useful tools within wider medical practice and are a valuable adjunct to diagnosis and therapy. The accurate visualization of anatomically and physiologically relevant information can frequently increase the accuracy of diagnosis made by a clinician and in doing so offer greater scope for the design of treatments on an individual basis. In addition to their more general use within traditional patient care, modern imaging methods play a vital role in treatment planning within several highly specialized branches of medicine.

Two particular clinical specialities in which treatment planning are important are radiotherapy and neurosurgery. The aim of radiotherapy is to treat pathological structures, usually malignant tumours, with radiation in such a way that the radiation dose to the pathological structure is maximized while the dose to the surrounding healthy tissue is minimized. Neurosurgery attempts to treat inter-cranial pathology by surgical means. Again, the aim is to maximize the efficacy of the surgical procedure while minimizing surgical damage to any surrounding or overlying healthy tissue. In both specialities known methods and techniques are used to formulate an effective treatment schedule which attempts this twofold object of treating the underlying pathology while sparing surrounding tissue.

When attempting any form of treatment planning the clinician will usually start with a defined volume of tissue, the treatment volume, requiring irradiation or excision, and will attempt to determine the path of entry of a clinically functional tool. In the case of radiotherapy treatment planning this clinically functional tool is usually a collimated beam of radiation and in the case of stereotactic neurosurgical planning it is a surgical instrument. In both cases the path taken by the clinically functional tool must travel the distance from the entry point on the surface of the body to the treatment volume and optimize the reduction of path length with the avoidance of critical physiological structures.

A method which aids the clinician in the identification of potential paths to an identified target in the field of stereotactic surgical planning is known from 3D Modelling for Computer-Assisted Neurosurgical Procedures by S. M. Krishnan et al., Biomedical Engineering, Applications, Basis and Communications, Vol. 7, No. 5, 1995. This describes a display format in which 8 sided geometrical volumes are used to segregate areas within the skull. The operator identifies target and critical volumes in the cranium and an 8 sided parallelopiped is constructed around each identified critical volume, the apex of each parallelopiped positioned at the centre of the target volume. The result is displayed in two views, one antero-posterior of the cranium and one caudal, including the 8 sided parallelepipeds. The operator selects potential entry points to the cranium on the skull surface outside the parallelopipeds. These entry points mark potential sites at which surgical instruments could be introduced into the skull cavity and pushed directly through to the target volume.

Each 8 sided parallelopiped, as described in the method, bounds the structure within a diamond shape consisting of 4 facets spanning the distance from the apex to the diamond face, the face itself consisting of a further 4 facets. As such it offers only a coarse attempt at isolating volumes within the cranium. The parallelepipeds do not track the contours of the critical volume which they bound, rather, they cordon off a four sided segment of the skin surface as being unsuitable for surgical entry, and if the geometry of the critical volume is complex then this bounding surface segment may be quite larger than it needs to be. In addition, the clinician is required to find a suitable spot on the surface of the volume by a process involving trial and error. No further information regarding the relationship between the surgical instrument and the target point is provided. Since only two views are presented the clinician himself is required to mentally orientate and arrange the spatial data within the 3 dimensional volume, keeping all geometrical relationships secure. The clinician is in effect required to learn another way of thinking about the physical structure under consideration.

It is an object of the invention to present the clinician with anatomical information in a form which is instantly recognizable and familiar, which provides information about the anatomical environment in relation to the treatment area and the skin surface and which provides a clear visualization of the route between the surface of the object and some target point within. This object is achieved by the method according to the invention, which is characterized in that a target centric projection is created by identifying a surface and projecting information from the target point onto the identified surface.

According to the method, a target point is identified. This target point is used as the point within the entire volume data set from which information is projected. This might normally be part of some target volume and in the case of treatment planning the target volume would be the volume representing the tissue volume to be treated. For instance the target volume might be a tumour requiring radiotherapy treatment or surgical excision. The target point would usually be the centre of the target volume but it is not always the case and in a particularly large target volume, for example, the clinician might wish to centre the projection method on some particular section of the target volume.

According to the invention a surface is identified within the object data set. This would normally be the surface of the imaged body, but need not necessarily be so. Information is projected radially from the target point outwards to the surface on which it can be represented. In this way the viewer is presented at each point on the surface with information that can represent the target point in its relationship to that point on the surface. That is to say, if the viewer were presented with an image showing the surface of the volume then the information projected onto that surface would communicate information about the target point with respect to each point on that surface.

These manipulations of the object data set take place within the central processor of a computer and the resulting images are viewed on a screen, usually a computer screen, in digital format. As such, the techniques of digitization already known in the art are applicable. For example, when a digital representational image is created, either from the physical process of imaging or from a process of abstract data manipulation, the information contained within the image is held as a series of discrete data points in an object data set. This object data set itself exists within wider multi-dimensional space. Each data point represents information held about a specific geometrical position within the original imaged object or within the space which the object data set represents. In the case of medical imaging, each data point describes some aspect of the imaged object or body, such as the relative density, X-ray opacity or water content at individual points throughout the tissue. This information is usually presented to the viewer in visual digital format, often as either an image of a 3 dimensional volume projected onto a viewing screen or as a series of 2 dimensional images representing slices from within the volume, each also presented onto a viewing screen.

Within any digitized two dimensional image presented on a screen, the totality of displayed information is shown as an array of pixels. Each pixel constitutes a small component of the overall image being shown and the data points from the object data set from which the image is derived are allocated into these pixels to form the image as seen. In this way the viewing of any 2 dimensional image can be appreciated as simply the viewing of a set of pixels. However, the object data set itself can be thought of as a set of pixels in a virtual space, or as a set of the 3 dimensional equivalent, voxels, and in this latter case contains all the information within the overall space described by the object data set. In this way, the production of an image on a screen can be appreciated as being simply the allocation of the information from within the individual virtual voxels into an array of pixels to be shown on a computer screen. The image shown on the screen could be, say, anatomical information as it would be seen at a particular slice through the original object or it could be a reconstructed image showing a representation of the 3 dimensional object as viewed from a certain angle.

As such, the identification of a target point and a surface within the original volume is analogous to identifying a point and a surface within the virtual object space representing the original volume, and vice versa. The target point chosen would normally be the point within the virtual object representing a point in the real object which would be at the centre of some volume to be treated. The surface chosen would normally correspond to the real surface of the original object, but need not necessarily do so. The essence of the invention as described in the claims can thus be seen to be projection of information outwards, from a point representing some real point in space, to a surface around or about that point.

In another embodiment, volumes of interest other than the target volume can be identified within the same object data set. For example, blood vessels may be segmented from the original object data set or physiologically important volumes may be identified by operator from within the original volume. Segmentation, known as such, is a method by which areas or volumes of interest within an image data set are identified and demarcated within the image. These segmented regions are usually rendered in a distinctive way, often using a different colour, shading or other distinctive marking, so that they become instantly recognizable within the image. Medical imaging has many uses for segmentation including the identification of lumbar vertebrae within images of the lower torso and the identification of the left ventricular cavity in physiological measurement. Alternatively, volumes within the image data may be manually identified by the operator, for example by mouse-clicking around the outside of the areas in several 2 dimensional cross sectional slices and then computationally interpolating through the intervening slices to delineate a subvolume within the overall object data set. In the case of the invention, the regions which are segmented or otherwise identified may be other critical structures within the volume of tissue that the data set represents. These could be volumes of tissue that the clinician wishes to avoid, in which case these critical structures might include major blood vessels and identifiable volumes of neurological tissue which control critical functions like speech or specific areas of motor function.

A functional method by which these volumes may be segmented would be to register, or combine within one image, two separate object data sets from two separate imaging modalities. For example, an object data set describing the head may be combined with a positron emission tomograph of the important functional parts of the brain. These two images may be registered, or combined, to give an overall image incorporating both anatomical and physiological information. The physiologically important regions within the skull would be identifiable and the information used to identify them would be used to segment these regions within the overall image. In the same manner an arteriograph can be used to identify the arteries within a tissue volume. This may then be registered with a detailed image of the same tissue volume from, say, a CT scanner to segment the major arteries within the tissue volume.

Information from these segmented regions within the skull can now be projected onto the identified surface as though being projected along linear rays emanating from the target point and travelling outwards in radial directions to the surface.

This information may simply be the existence or otherwise of the critical structures. If this is the case, then the resulting image shows the positions of all the critical structures projected onto the identified surface within the object data set, with respect to the position of the target point.

By creating a projection in this manner the clinician is presented with an image which shows the surface of body and projected onto it, the positions of any segmented or identified regions as seen from the target point. Essentially these regions, or critical structures, are simply any volumes within the object data set which the user has deemed to be of interest. When these regions are regions critical to the healthy functioning of the overall organism, the image of the surface as presented also includes a projection of physiologically critical areas. In essence, the projection reveals the points around the surface of the 3 dimensional volume from which a clear, straight path can be devised to the centre of the target volume without traversing any part of any critical structure. In this way, the image presents the user or clinician with the safe routes from the surface to the target point.

Claim 4 defines a method in which the critical structures are enlarged in size within the object data set. When the target centric projection is created it will now contain projections of the critical structures which are larger than in the original object data set. This has the effect of allowing the clinician or user a margin of error in identifying safe routes from the surface of the 3 dimensional volume to the target point.

In another embodiment of the invention, the information projected from the target point to the identified surface is information about the distance between the target point and each point on the identified surface. In this way information about the depth of the target point within the volume of tissue represented by the object data set can be projected onto the identified surface. This information allows the clinician to identify the shortest routes to the target point and so plan a treatment which minimizes damage to surrounding healthy tissue.

In a further embodiment of the invention, the projection is created around a single point on the identified surface. For example, a planar projection may be created within a finite area around a point on the identified surface instead of over the whole identified surface.

In order to enhance the usefulness of the present invention the planar projection may be shown in combination with the volume information from the object data set from which it has been reconstructed. This is included in an embodiment of the invention in which the image of the planar projection is displayed together with the image of the multi-dimensional volume in such a way that the planar projection is superimposed onto the image of the volume about the point on the identified surface around which the planar projection has been created. If both images are then shown with the same angular orientation on a viewing screen, the viewer is presented with a view of the finite planar projection showing the projected information for a small area superimposed onto the surface of the volume. This may then be handled graphically and orientated as a complete whole so that if the image of the 3 dimensional volume were rotated or revolved then the 2 dimensional planar projection would rotate and revolve with it. The planar projection may therefore not always be seen as a flat 2 dimensional image, but will often be rendered on the viewing screen as though it is tilted or tipped at an angle within the screen.

The sum total of potential points situated on the identified surface within the object data set can be dichotomized into 2 separate groups. One group is the group of points on the surface which offer a clear rectilinear pathway to the target point. The other group is the group of points on the surface which offer a rectilinear pathway to the target point which does traverse some part of an identified critical volume at some point along its length.

In further embodiments of the invention, these two groups of selected points are calculated. This provides the clinician with two groups of potential entry points into the volume for a clinically functional tool. One group of points, the points which lead to rectilinear pathways which do not traverse any part of any critical volume offer a safe route to the target. The other group, those that reveal rectilinear pathways that pass through some part of any critical volume, offer unsafe, or less desirable routes to the target. These two groups of points may be presented to the user graphically as, say, an image of the original volume with the two groups of points mapped on the surface in two visually distinctive ways, or may be presented non-graphically as simply as two groups of co-ordinates.

When a target centric projection has been created it is possible to orient the information within the object data set to present the user with various information and image formats. In another embodiment of the invention, the pathway from any point on the identified surface to the target point is shown within the image. This allows the clinician or user to select any point on the identified surface and be presented with an image showing the target point, the projection onto the identified surface, a point selected on this surface and the rectilinear pathway which spans the distance between the selected point and the target point. This allows the user to view the pathway in relation to the surrounding anatomy. As with any other image, the orientation of the volume together with the selected points and the pathway may be altered by rotation, enlargement and any other image manipulation.

The invention also relates to a computer program as defined in claim 11 and a workstation as defined in claim 12.

These and other aspects of the invention will be further elucidated and described with reference to the drawings.

FIG. 3 shows the essential idea of the invention which is to project information from some target point within an object data set. This figure shows a chosen target point, 31, some surface, 32 within the image and information projected radially from the target point, depicted by rays, 33.

Figure 4:
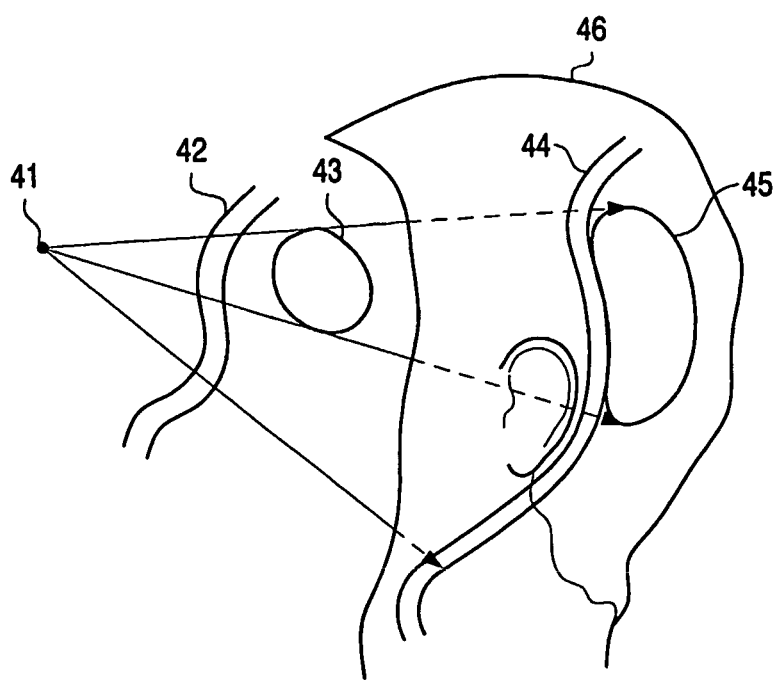
FIG. 4 shows the target point with the addition of critical structures and the projection of the positions of these critical structures onto the identified surface.

FIG. 4 shows the projection from the target point 41 to a surface 46 of information which indicates the existance of critical structures 42 and 43. In this case 42 may be a blood vessel and 43 some region of the brain which is critical for normal functioning. These are projected onto the surface as regions 44 and 45 respectively.

Figure 1:
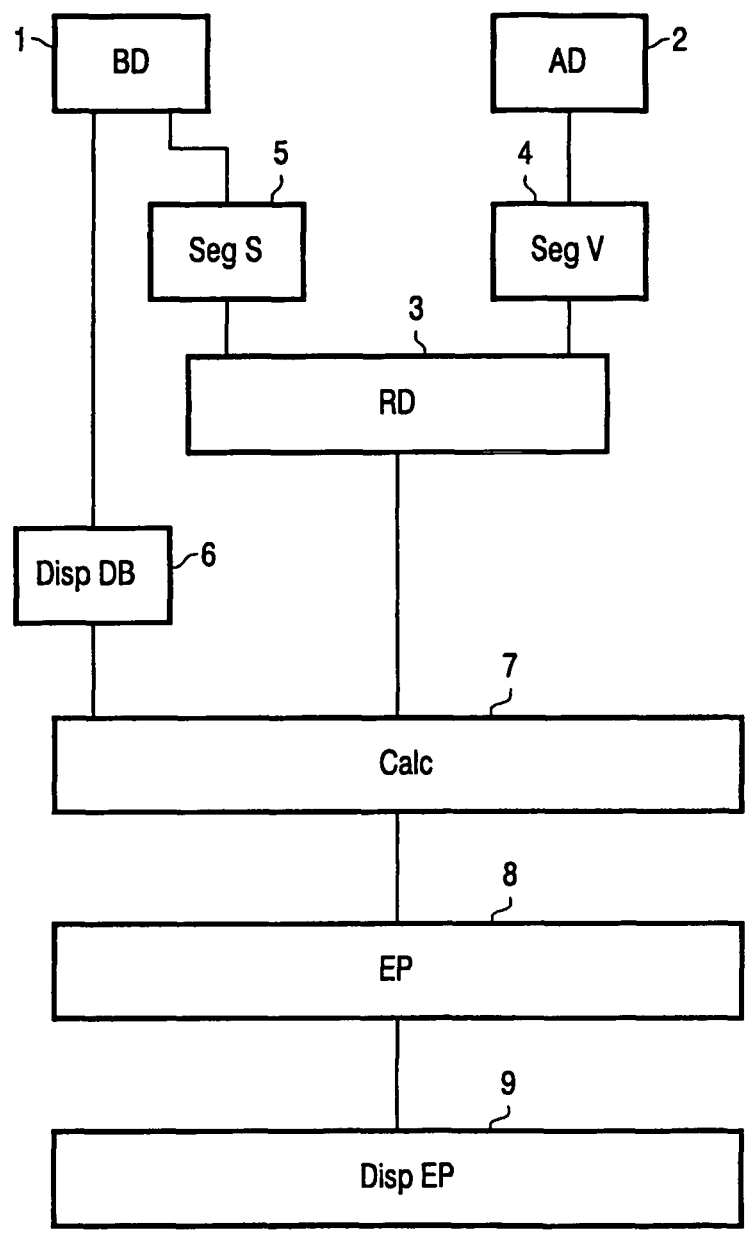
FIG. 1 is a flow diagram describing an embodiment of the invention.
Figure 2:
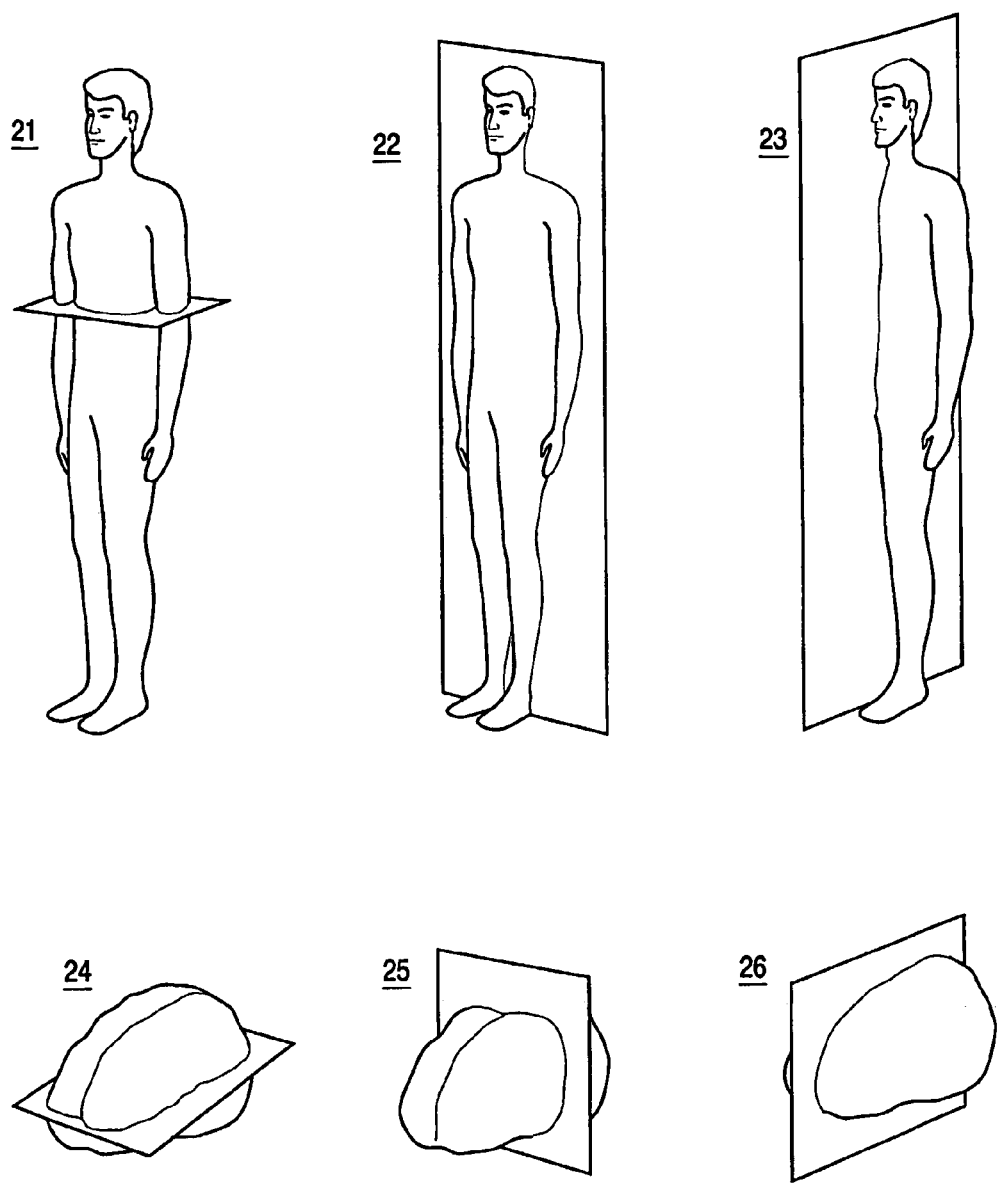
FIG. 2 shows the orientations of transverse, coronal and sagittal slices through the body.
Figure 3:
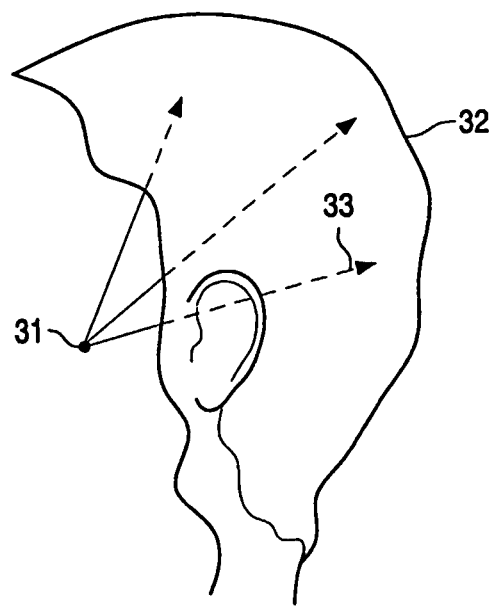
FIG. 3 shows the projection of information from the target point to an identified surface.

FIG. 1 shows an embodiment by which the invention may be utilized in practice. In this embodiment two data sets, a dataset 1 describing a brain, BD, and a dataset 2 containing angiographic data, AD, are registered, 3, RD. AD contains information about the position of the major arteries within the skull and these can be segmented, SegV, 4. In this case, the identified surface as required in the invention is the surface of the skull and this can also be segmented, SegS, 5. The data sets can be displayed in a number of ways. The method of multi-planar reformatting, which produces 2 dimensional images known as multi-planar reformats (MPRs) is a known method by which the information held in the object data set can be displayed as a series of 2 dimensional slices that are orientated at any angle within the 3 dimensional volume. In this way the resulting images can be viewed in slices which are reconstructed at any angular orientation within a complete $2\pi$ solid angle. In particular, the object data set can be displayed in any one of three mutually orthogonal directions so that the image data is presented as a series of transverse slices perpendicular to a line running along the axis of the body from head to foot, 21, as a series of coronal slices perpendicular to a line running from the posterior surface of the body to the anterior surface, 22, and as a series of sagittal slices perpendicular to a line running from the left side of the body to the right side, 23. The same orientations as applied to the brain are shown in FIG. 2, 24, 25, 26. The brain data set, BD, is displayed in all three of these orientations in an orthoviewer, 6, which is a split screen combination showing three separate views of the object data set. A target point is selected by the user in the orthoviewer, 6, and all three views show the multi-planar reformat slice at the depth through the object data set which includes that selected point. Once the target point is selected the projection can be calculated, Calc, 7. At this point the projection of the vessels in AD from the target point is calculated and is shown in a surface rendered view. The user can then define a selected point, EP, 8, on the identified surface, as a possible entry point to the volume and the combined dataset including the projection data, the target point, the selected point and the pathway between the target point and the selected point is displayed, DispEP, 9. The pathway between the selected point on the surface and the target point can be shown in the image as a needle.

Figure 5:
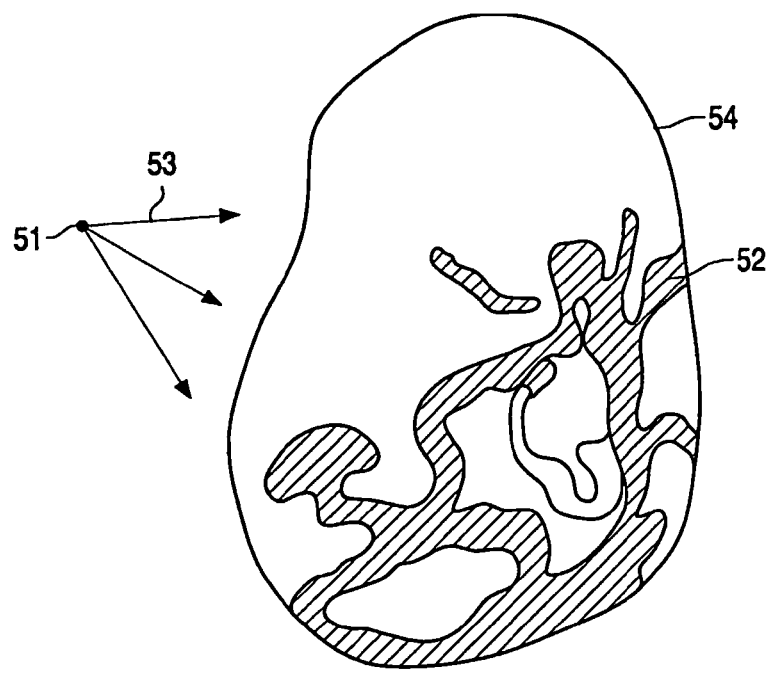
FIG. 5 shows a projection of blood vessels as created by the embodiment.

The surface of the skull is now shown with the projections of the positions of the segmented blood vessels 52 as related to the position of the target point 51. This is shown in FIG. 5 which shows information projected radially 53 from the target point towards the surface 54. This image can now be used by the clinician to examine the head to assess possible entry routes into the skull which intersect with the target point while bypassing the blood vessels. If an attempt is made to enter the skull with any clinically functional tool and approach the target point through any part of any blood vessel projection then the route taken by the tool will traverse some part of the segmented blood vessel. The entire image representation system represents the original skull and the manipulations that might occur in real life, so this would mean that if that point on the surface were used as the real point of entry on the original skull then the path taken by the clinically functional tool would traverse the real blood vessel inside the skull. If any other type of critical volume were projected onto the skull surface instead of blood vessels the same would hold true. The overall system then can be used to assess routes through to a target point within the body which avoid critical structures.

If the segmented blood vessels or any other critical structure were also enlarged as defined in claim 4 within the object data set then the areas of the skull surface covered by the projections would also increase. The would reduce the size of the remaining surface area left and number of possible entry routes to the target point would be reduced. At the same time however, the areas left available offering sites of potential entry now only include potential entry points which have a built in minimum safe distance away from any critical volume. Not all critical volumes may be enlarged and some individual critical volumes may be enlarged more or less than others. This function may be used for example when both blood vessels and physiologically important cranial volumes such as speech areas are projected onto the skull surface. The blood vessels may be projected from their original size within the object data set but a segmented or identified volume controlling speech may be enlarged prior to projection to give a greater margin of safety within the image around that particular part of the organ.

Figure 6:
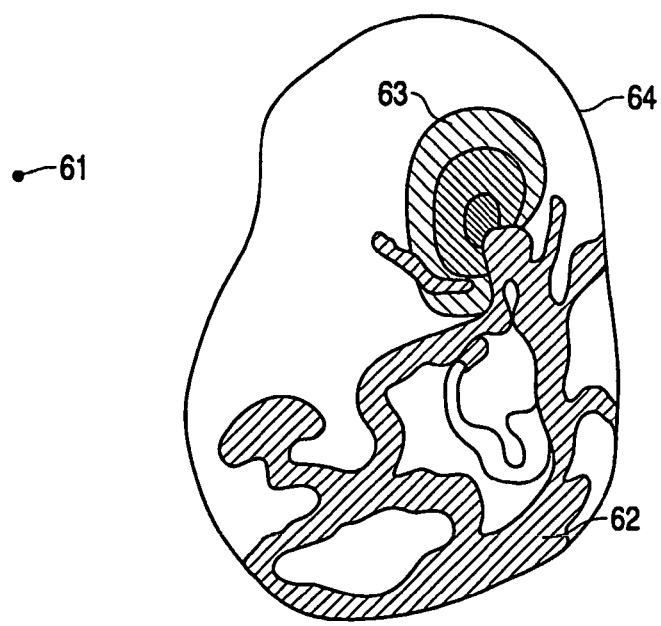
FIG. 6 shows a projection of blood vessels as created by the embodiment including distance information presented as a dartboard.

The image of the head, including the projections can be rotated on the viewing screen and viewed from any angle. FIG. 6 shows distance information projected from the target 61 onto the skull surface 64 and rendered distinctively 63 so that the points on the skull surface closest to the selected target point are displayed in one colour, and points at various distances further away are rendered in other colours. Because the surface of the skull is essentially rounded, the display of these colours tends towards a set of concentric circles, although this may not necessarily be true at all points around the skull surface. This projection may be seen concurrently with the projection of critical volumes, 62.

Figure 7:
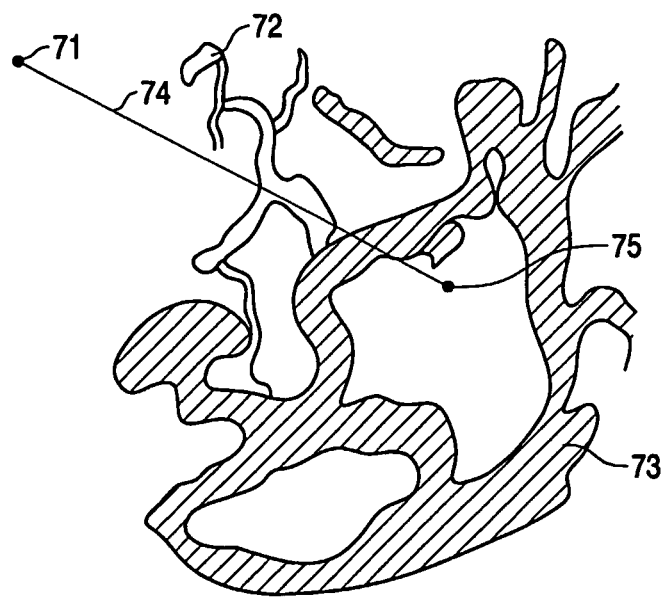
FIG. 7 shows the skull with surface removed to reveal target point, segmented structures, selected point on the surface and rectilinear pathway from this point to the target point.

The user can now choose several potential entry points to the skull for surgical instruments or beams of radiation. Once a potential entry point has been selected, the pathway between the potential entry point and the target point can be shown within the image. For example, the skin and skull surface can be removed from the image to show only the target point 71, the segmented vessels 72 and their projection 73, the selected entry point 75 and the pathway 74 between this and the target point. FIG. 7 shows this embodiment.

Figure 8:
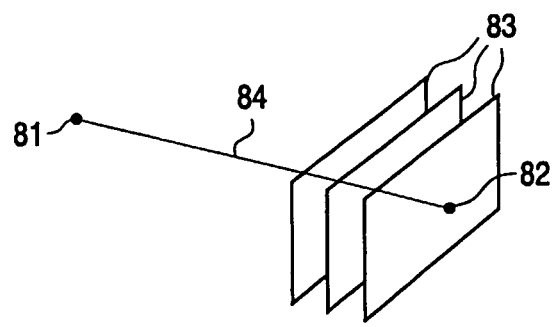
FIG. 8 shows MPRs transverse to the rectilinear pathway.

Once a possible entry point on the surface has been selected the 3 dimensional volume data set can be reformatted to present the information in a series of slices centred around the rectilinear pathway between the point on the surface and the target point. These multi-planar reformats 83 display the image data contained within the volume at the orientation it would be seen at if the observer were able to follow the rectilinear pathway 84 from the point on the surface 82 to the target point 81. This is shown in FIG. 8. This allows the clinician to view the image data contained within the volume along the rectilinear pathway. This would enable the clinician to verify the position of the pathway relative to the local anatomy.

Figure 9:
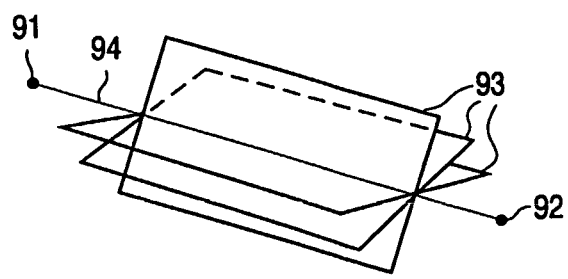
FIG. 9 shows MPRs which contain the rectilinear pathway.

The object data set may also be reformatted to present the information in a series of 2 dimensional slices which revolve about the rectilinear pathway 93. In this case the slices are reformatted so that they are orientated along the direction of the rectilinear pathway 94 at any angulation, with each slice containing the rectilinear pathway as a bisector which divides the 2 dimensional image into two halves of equal area. Since these slices may be reconstructed at any angulation around the rectilinear pathway they form a series of images which when scrolled provide a view around the rectilinear pathway. This embodiment is shown in FIG. 9. The target point 91 and the selected point on the surface 92, may or may not be included, either separately or together.

Figure 10A:
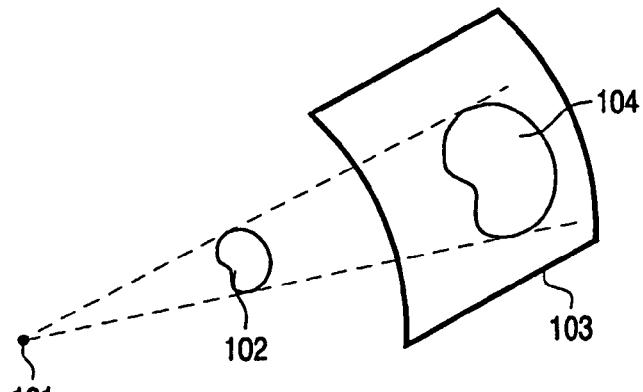
FIG. 10 shows the projection of enlarged critical structures onto the identified surface.
Figure 10B:
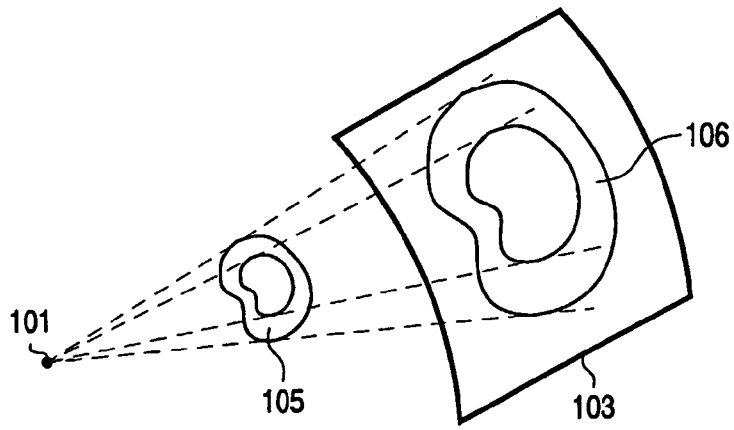

FIG. 10 shows the projection of enlarged critical structures 105 from the target point 101 onto the identified surface 103 as defined in claim 4. The increase in size of the critical volumes from 102 to 105 can be set automatically by the system or set manually by the user. The result is an enlarged projection, from 104 to 106.

Figure 11:
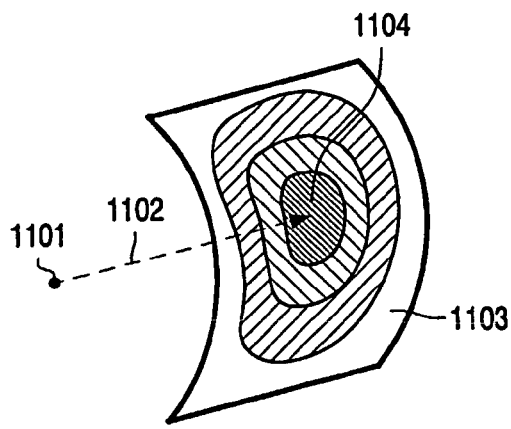
FIG. 11 shows the projection of distance information onto the identified surface.

FIG. 11 shows the projection of information 1104 describing the distance 1102 between the target point 1101 and the identified surface 1103 as defined in claim 5.

Figure 12:
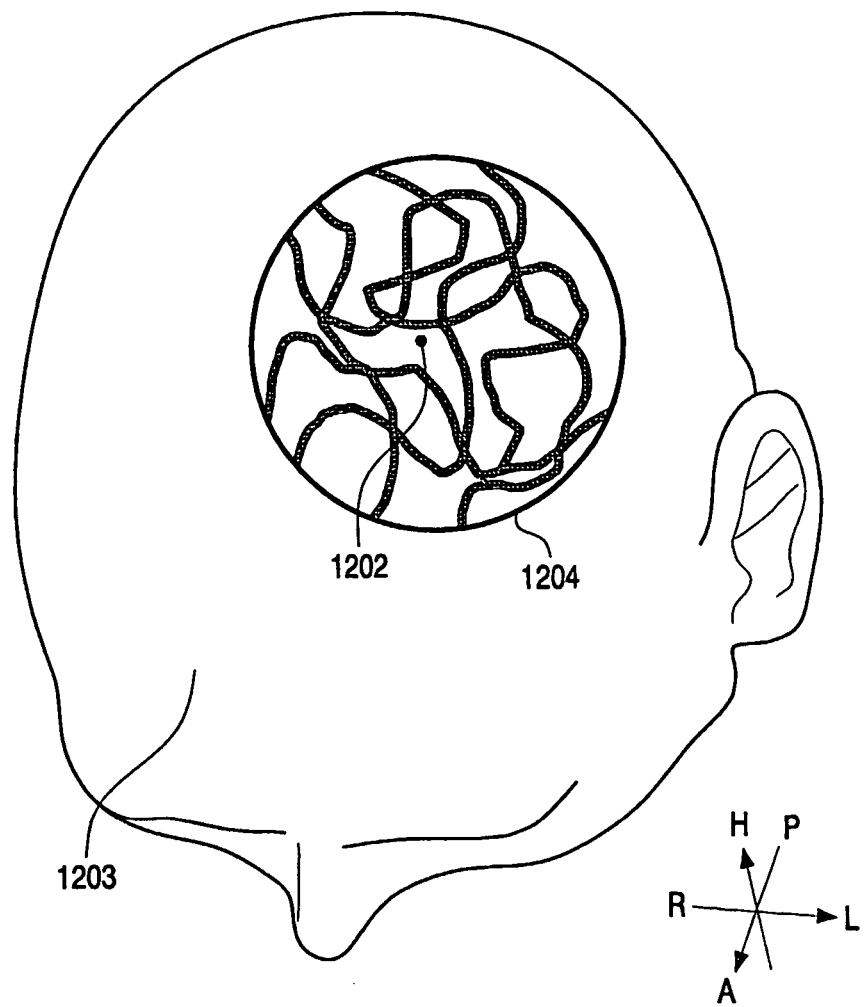
FIG. 12 shows the projection of a planar projection about a selected point on the identified surface.

FIG. 12 shows the creation of a planar projection 1204 about a selected point 1202 on an identified surface 1203. FIG. 12 shows the planar projection combined with the view of the identified surface. In this image the planar projection shows only blood vessels but could also show other types of critical volume.

The invention claimed is:

1. A method of producing and displaying an image of a multi-dimensional volume, from a multi-dimensional object data set, the method comprising the acts of:
    identifying an interior target point within the multi-dimensional volume;
    creating a plurality of simultaneous target centric projection paths by identifying an exterior surface and simultaneously projecting of information from the interior target point onto the identified exterior surface;
    projecting onto the identified exterior surface information describing a distance between the interior target point and the identified exterior surface of the multi-dimensional volume;
    identifying a critical structure within the multi-dimensional volume;
    projecting onto the identified exterior surface information from the critical structure; and
    enlarging the identified critical structure in volume prior to projection onto the identified surface so that only the identified critical structure is enlarged without enlarging a remainder of the identified surface.

2. The method as claimed in claim 1, further comprising the act of projecting onto a surface of the critical structure the information from the critical structure.

3. The method as claimed in claim 1, wherein a target centric projection path is created around a selected point on the identified exterior surface of the multi-dimensional volume.

4. The method as claimed in claim 3, further comprising the act of displaying the target centric projection path together with the multi-dimensional volume, in such a way that a displayed angular orientation of the target centric projection is the same as a displayed angular orientation of the multi-dimensional volume.

5. The method as claimed in claim 1, further comprising the act of calculating a collection of allowed points on the identified exterior surface, wherein none of the allowed points are coincident with the projection of the critical structure.

6. The method as claimed in claim 1, further comprising the act of calculating a collection of forbidden points on the surface of the volume, which are coincident with the projection of the critical structure.

7. The method as claimed in claim 1, further comprising the acts of:
   selecting a point on an identified surface of the multi-dimensional volume; and
   determining a rectilinear pathway from the selected point to the interior target point.

8. A computer program encoded on a computer readable medium for causing the computer to execute a method to produce and display an image of a multi-dimensional volume, from a multi-dimensional object data set, and causing the computer to perform the acts of:
   identifying and interior target point within the multi-dimensional volume;
   creating a plurality of simultaneous target centric projection paths by identifying an exterior surface and simultaneously projecting a plurality of information from the interior target point onto the identified exterior surface;
   projecting information describing the distance between the interior target point and the identified exterior surface of the multi-dimensional volume onto the identified exterior surface;
   identifying a critical structure within the multi-dimensional volume;
   projecting onto the identified exterior surface information from the critical structure; and
   enlarging the identified critical structure in volume prior to projection onto the identified surface so that only the identified critical structure is enlarged without enlarging a remainder of the identified surface.

9. A workstation configured for the purposes of displaying and using images comprising a computer program encoded on a computer readable medium for causing the computer to perform the acts of:
   identifying an interior target point within the multi-dimensional -volume;
   creating a plurality of simultaneous target centric projection paths by identifying an exterior surface and simultaneously projecting a plurality of information from the interior target point onto the identified exterior surface;
   projecting information describing the distance between the interior target point and the identified exterior surface of the multi-dimensional volume onto the identified exterior surface;
   identifying a critical structure within the multi-dimensional volume;
   projecting onto the identified exterior surface information from the critical structure; and
   enlarging the identified critical structure in volume prior to projection onto the identified surface so that only the identified critical structure is enlarged without enlarging a remainder of the identified surface.

* * * * *